United States Patent [19]
Simon et al.

[11] Patent Number: 6,005,094
[45] Date of Patent: Dec. 21, 1999

[54] OLIGONUCLEOTIDE ANALOGUES HAVING IMPROVED STABILITY AT ACID PH

[75] Inventors: Lionel N. Simon, Solana Beach, Calif.; Paul S. Miller, Baltimore; Paul O. P. Ts'o, Ellicott City, both of Md.

[73] Assignees: Genta Incorporated, San Diego, Calif.; The Johns Hopkins University, Baltimore, Md.

[21] Appl. No.: 08/364,840

[22] Filed: Dec. 27, 1994

Related U.S. Application Data

[63] Continuation of application No. 08/235,128, Apr. 28, 1994, abandoned, which is a continuation of application No. 08/001,109, Jan. 6, 1993, abandoned, which is a continuation-in-part of application No. 07/558,338, Jul. 27, 1990, abandoned, which is a continuation-in-part of application No. 06/924,234, Oct. 28, 1986, abandoned.

[51] Int. Cl.$^6$ ............................................. C07H 21/02
[52] U.S. Cl. ................. 536/24.5; 536/24.3; 536/23.1; 536/25.3; 536/25.1; 536/25.2; 514/44; 435/6
[58] Field of Search ................. 514/44; 536/24, 536/500, 25, 300

[56] References Cited

U.S. PATENT DOCUMENTS

| | | | |
|---|---|---|---|
| 4,839,177 | 6/1989 | Colombo et al. | 424/482 |
| 5,135,917 | 8/1992 | Burch | 514/44 |

OTHER PUBLICATIONS

Agrawal et al., "Absorption, Tissue Distribution and In Vivo Stability in Rats of a Hybrid Antisense Oligonucleotide Following Oral Administration," *Biochemical Pharmacology* 50(4):571–576 (1995).

Agrawal, "Antisense oligonucleotides: towards clinical trials," *TIBTECH* 14:376–387 (Oct. 1996).

Agrawal et al., "Pharmacokinetics, biodistribution, and stability of oligodeoxyncleotide phosphorothioates in mice," *Proc. Natl. Acad. Sci. USA* 88:7595–7599 (Sep. 1991).

Bennett et al., "Cationic Lipids Enhance Cellular Uptake and Activity of Phosphorothioate Antisense Oligonucleotides," *Molecular Pharmacology* 41:1023–1033 (1992).

Bishop et al., "Phase I Trial of an antisense Oligonucleotide OL(1)p53 in Hematologic Malignancies," *Journal of Clinical Oncology* 14(4):1320–1326 (Apr. 1996).

Ts'o et al., "An Approach to Chemotherapy Based on Base Sequence Information and Nucleic Acid Chemistry," *Biological Approaches to the Controlled Delivery of Drugs* 507:220–241 (1987).

Webb et al., "BCL–2 antisense therapy in patients with non–Hodgkin lymphoma," *The Lancet* 349:1137–1141 (1997) (Apr. 19, 1997).

Krieg et al., "CpG Motifs in Bacterial DNA Trigger Direct B–Cell Activation," *Nature*, 374, 546–549 (Apr. 6, 1995).

Gura, "Antisense Has Growing Pains—Efforts to Develop Antisense Compounds as Therapies for Cancer, AIDS, and Other Diseases Have Encountered Some Unexpected Questions About How the Drugs Really Work," *Science*, 270, 575–577 (1995).

Havesi et al., "Contribution to the Mechanism of the Acid–Catalyzed Hydrolysis of Purine Nucleosides," *J. Am. Chem. Soc.*, 94(13), 4715–4720 (1972).

Abstract of Nielsen et al.(I), *Nature*, 365, 566 (1993) entitled "'Peptide' nucleic acid hybridizes to complementary oligonucleotide," *Chem. Eng. News*, 71(41), 25 (Oct. 11, 1993).

Egholm et al., "PNA Hybridizes to Complementary Oligonucleotides Obeying the Watson–Crick Hydrogen Bonding Rules," *Nature*, 365, 566 (1993); original publication referred to in reference "S" supra.

R. S. Root–Bernstein(I), "AIDS Is More Than HIV: Part I," *Genetic Engineering News*, Sep. 1, 1992, pp. 4–6.

R. S. Root–Bernstein(II), "AIDS Is More Than HIV: Part II," *Genetic Engineering News*, Sep. 15, 1992, pp. 4–5.

Nielsen et al.(II), "Sequence Selective Recognition of DNA by Strand Displacement with a Thymine–Substituted Polymide," *Science*, 254, 1497–1500 (1991).

Zon, "Oligonucleotide Analogues as Potential Chemotherapeutic Agents," *Pharmaceutical Research*, 5(9), 539–549 (1988).

T. Beardsley, "Trends in Cancer Epidemiology—A War Not Won," *Scientific American*, 270(1), 130–138 (1994).

*Primary Examiner*—John Kight
*Assistant Examiner*—L. Eric Crane
*Attorney, Agent, or Firm*—Lyon & Lyon LLP

[57] ABSTRACT

Acid resistant Oligomers suitable for oral administration, orally acceptable formulations of such Oligomers and preparation of pharmaceutical formations of such Oligomers are provided.

15 Claims, 7 Drawing Sheets

** 2' OMe MP data corrected for depurination of 3' terminal deoxyadenosine.

** 2' OMe MP data corrected for depurination of 3' terminal deoxyadenosine.

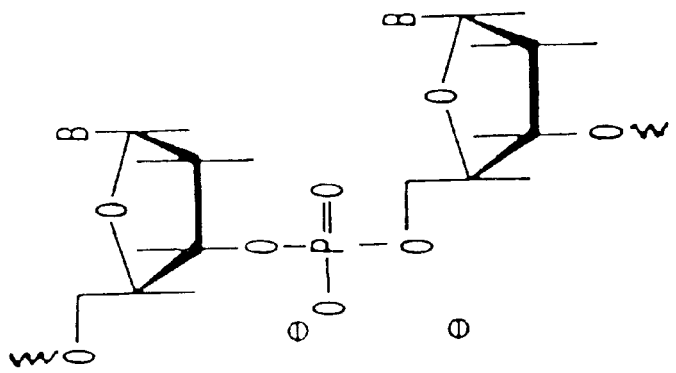
Fig. 8C  OLIGODEOXYRIBONUCLEOSIDE
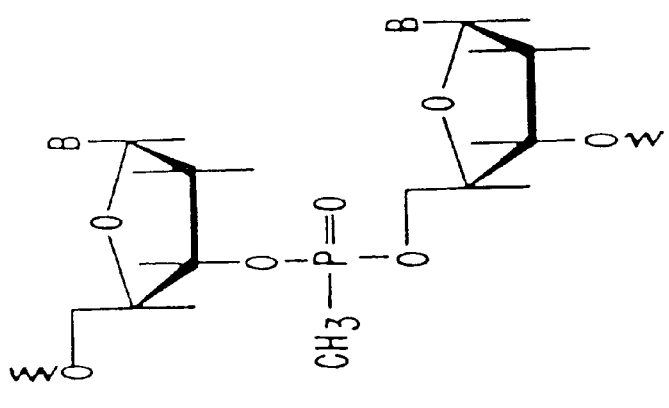
Fig. 8B  OLIGODEOXYRIBONUCLEOSIDE METHYLPHOSPHONATE
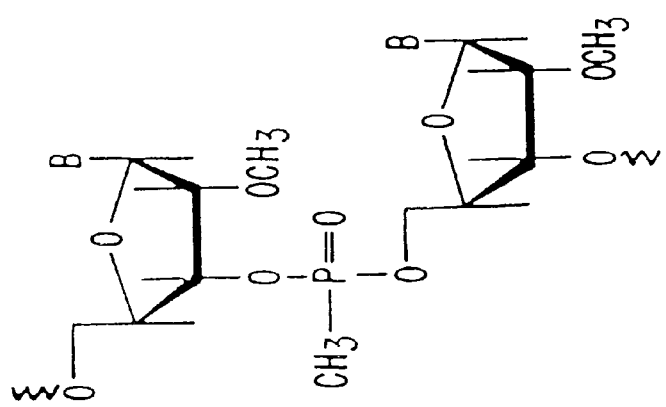
Fig. 8A  OLIGO-2'-O-METHYLRIBONUCLEOSIDE METHYLPHOSPHONATE 6,005,094

OLIGONUCLEOTIDE ANALOGUES HAVING IMPROVED STABILITY AT ACID PH

CROSS-REFERENCE TO RELATED APPLICATIONS

This application is a continuation of application Ser. No. 08/235,128, filed Apr. 28, 1994, abandoned, which is a continuation of Ser. No. 08/001,109, filed Jan. 1, 1993, abandoned which is a continuation-in-part of U.S. Ser. No. 07/558,338, filed July 27, 1990 ABN, which is a continuation-in-part of U.S. Ser. No. 06/924,234, filed Oct. 28, 1986, ABN, the disclosures of which are incorporated herein by reference.

BACKGROUND AND INTRODUCTION TO THE INVENTION

The present invention is directed to methods of providing Oligomers which exhibit improved stability at acid pH, to methods of delivering such Oligomers to their sites of action and to their use in formulations for oral administration or other dosage forms where acid resistance is advantageous.

Depurination (loss of the purine bases from nucleosidyl units through cleavage of the glycosidic bond between the base and sugar) of deoxyribonucleic acid (DNA) under acidic conditions has been reported. (Hevesi, L., et al., *J. Amer. Chem. Soc.*, 94, 4715–4720 (197). The oral delivery of therapeutic oligodeoxyribonucleotides may require exposure of the drug to the acidic conditions of the stomach (about pH 1) for up to about 4 hours under normal conditions of drug delivery and under conditions of sustained released drug delivery (see, e.g., U.S. Pat. No. 4,839,177), for up to about 12 hours. Due to its lack of stability under acid conditions, it is unlikely that enough of an orally administered oligodeoxynucleotide would remain intact to be effective. Ribonucleic acid (RNA) has been reported to be significantly more stable to depurination under acidic conditions than its DNA counterpart reportedly because of the apparent stabilizing effect of the 2' hydyoxyl on the glycosidic bond between sugar and the base (Hevesi, L., et al., *supra*).

Although RNA may be resistant to depurination under acid conditions, its sensitivity to ubiquitous nucleases present in biological materials limits its therapeutic usefulness. Furthermore, the use of oligoribonucleotides as a drug in its unmodified form is not feasible because of the inherent instability of the molecule to neutral to mildly basic conditions.

Unfortunately, protection of the RNA against nucleases by replacing the phosphate linkages with methylphosphonates is not possible because the 2'-hydroxyl of the sugar rapidly cleaves the methylphosphonate backbone.

SUMMARY OF THE INVENTION

The present invention is directed to methods of providing Oligomers which comprise nucleosidyl units having a preselected base sequence in an acid resistant form. According to one aspect of the present invention Oligomers are provided wherein the nucleosidyl units have a sugar moiety which is a 2'-O-alkyl ribosyl group. Preferably the Oligomer is substantially neutral. Preferred are Oligomers having methylphosphonate internucleosidyl linkages more preferably from about 50 percent to about 100 percent of the internucleosidyl linkages are methylphosphonate linkages. Preferred 2'-O-alkyl ribosyl groups include 2'-O-methyl ribosyl groups.

According to an alternate aspect, the Oligomers provided in acid resistant form comprise methylphosphonate internucleosidyl linkages, preferably from about 50 percent to about 100 percent methylphosphonate linkages.

According to an additional aspect, the present invention is directed to methods of preparing an Oligomer which comprises nucleosidyl units having a preselected base sequence which Oligomer is suitable for oral administration and exhibits resistance to acid degradation. According to one aspect this method comprises synthesizing the Oligomer using nucleosidyl units having a sugar moiety which is a 2'-O-alkylribosyl group, more preferably a 2'-O-methyl ribosyl group. Preferably the Oligomer is substantially neutral. More preferably the Oligomer is synthesized to have methylphosphonate internucleosidyl units.

Alternatively, the method comprises synthesizing the Oligomer using nucleosidyl units having methylphosphonate internucleosidyl linkages. Particularly preferred are Oligomers having from about 50 percent to about 100 percent methylphosphonate internucleosidyl units.

In a further aspect, the present invention is directed to a method of orally delivering an Oligomer to a mammal for therapeutic purposes wherein said Oligomer comprises a nucleosidyl unit having a purine base which method comprises administration of an acid resistant Oligomer. According to one embodiment of this aspect the acid resistant Oligomer comprises nucleosidyl units having a sugar moiety which comprises a 2'-O-alkyl ribosyl group, preferably a 2'-O-methylribosyl group. Preferably the Oligomer is substantially neutral. Preferred acid resistant Oligomers include Oligomers having methylphosphonate internucleosidyl linkages, more preferably from about 50 percent to about 100 percent of the internucleosidyl linkages are methylphosphonate linkages. According to an especially preferred aspect, the acid resistant Oligomer is administered in a controlled-rate release form.

Among other factors, the present invention is based on our surprising finding that Oligomers which are synthesized to incorporated nucleosidyl units having a sugar moiety which is a 2'-O-alkyl ribosyl group or which incorporate methylphosphonate internucleosidyl linkages exhibit advantageous resistance to acid catalyzed depurination and subsequent hydrolysis.

It is also believed that the Oligomers which comprise nucleosidyl units having a 2'-O-alkylribosyl group and methylphosphonate internucleosidyl linkages appear to form more stable duplexes with an RNA target molecule than do the corresponding 2'-deoxy-ribonucleoside methylphosphonates.

According to a further aspect, the present invention is directed to pharmaceutical compositions which comprise an acid resistant Oligomer of the present invention in a controlled-rate release form. Alternatively, pharmaceutical compositions comprising an acid resistant Oligomer are provided which compositions are acidic themselves or which may be exposed to acidic conditions during manufacture or storage.

Definitions

As used herein, the following terms have the following meanings unless expressly stated to the contrary.

The term "purine" or "purine base" includes not only the naturally occurring adenine and guanine bases, but also modifications of those bases such as bases substituted at the 8-position, or guanine analogs modified at the 6-position or the analog of adenine, 2-amino purine, as well as analogs of purines having carbon replacing nitrogen at the 9-position such as the 9-deaza purine derivatives and other purine analogs.

The term "nucleoside" includes a nucleosidyl unit and is used interchangeably therewith, and refers to a subunit of a nucleic acid which comprises a 5-carbon sugar and a nitrogen-containing base. The term includes not only those nucleosidyl units having A, G, C, T and U as their bases, but also analogs and modified forms of the naturally-occurring bases, including the pyrimidine-analogs such as pseudoisocytosine and pseudouracil and other modified bases (such as 8-substituted purines). In RNA, the 5-carbon sugar is ribose; in DNA, it is a 2'-deoxyribose. The term nucleoside also includes other analogs of such subunits, including those which have modified sugars such as 2'-O-alkyl ribose.

The term "phosphonate" refers to the group

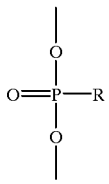

wherein R is hydrogen or an alkyl or aryl group. Suitable alkyl or aryl groups include those which do not sterically hinder the phosphonate linkage or interact with each other. The phosphonate group may exist in either an "R" or an "S" configuration. Phosphonate groups may be used as internucleosidyl phosphorus group linkages (or links) to connect nucleosidyl units.

The term "phosphodiester" or "diester" refers to the group

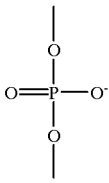

wherein phosphodiester groups may be used as internucleosidyl phosphorus group linkages (or links) to connect nucleosidyl units.

A "non-nucleoside monomeric unit" refers to a monomeric unit wherein the base, the sugar and/or the phosphorus backbone has been replaced by other chemical moieties.

A "nucleoside/non-nucleoside polymer" refers to a polymer comprised of nucleoside and non-nucleoside monomeric units.

The term "oligonucleoside" or "Oligomer" refers to a chain of nucleosides which are linked by internucleoside linkages which is generally from about 4 to about 100 nucleosides in length, but which may be greater than about 100 nucleosides in length. They are usually synthesized from nucleoside monomers, but may also be obtained by enzymatic means. Thus, the term "Oligomer" refers to a chain of oligonucleosides which have internucleosidyl linkages linking the nucleoside monomers and, thus, includes oligonucleotides, nonionic oligonucleoside alkyl- and aryl-phosphonate analogs, alkyl- and aryl-phosphonothioates, phosphorothioate or phosphorodithioate analogs of oligonucleotides, phosphoramidate analogs of oligonucleotides, neutral phosphate ester oligonucleoside analogs, such as phosphotriesters and other oligonucleoside analogs and modified oligonucleosides, and also includes nucleoside/non-nucleoside polymers. The term also includes nucleoside/nucleotide polymers wherein one or more of the phosphorus group linkages between monomeric units has been replaced by a non-phosphorous linkage such as a formacetal linkage, a thioformacetal linkage, a sulfamate linkage, or a carbamate linkage. It also includes nucleoside/non-nucleoside polymers wherein both the sugar and the phosphorous moiety have been replaced or modified such as morpholino base analogs, or polyamide base analogs. It also includes nucleoside/non-nucleoside polymers wherein the base, the sugar, and the phosphate backbone of the non-nucleoside are either replaced by a non-nucleoside moiety or wherein a non-nucleoside moiety is inserted into the nucleoside/non-nucleoside polymer. Optionally, said non-nucleoside moiety may serve to link other small molecules which may interact with target sequences or alter uptake into target cells.

The term "alkyl- or aryl-phosphonate Oligomer" refers to Oligomers having at least one alkyl- or aryl-phosphonate internucleosidyl linkage. Suitable alkyl-or aryl- phosphonate groups include alkyl- or aryl-groups which do not sterically hinder the phosphonate linkage or interact with each other. Preferred alkyl groups include lower alkyl groups having from about 1 to about 6 carbon atoms. Suitable aryl groups have at least one ring having a conjugated pi electron system and include carbocyclic aryl and heterocyclic aryl groups, which may be optionally substituted and preferably having up to about 10 carbon atoms.

The term "methylphosphonate Oligomer" (or "MP-Oligomer") refers to Oligomers having at least one methylphosphonate internucleosidyl linkage.

The term "neutral Oligomer" refers to Oligomers which have nonionic internucleosidyl linkages between nucleoside monomers (i.e., linkages having no positive or negative ionic charge) and include, for example, Oligomers having internucleosidyl linkages such as alkyl- or aryl- phosphonate linkages, alkyl- or aryl-phosphonothioates, neutral phosphate ester linkages such as phosphotriester linkages, especially neutral ethyltriester linkages; and non-phosphorus-containing internucleosidyl linkages, such as sulfamate, morpholino, formacetal, thioformacetal, and carbamate linkages. Optionally, a neutral Oligomer may comprise a conjugate between an oligonucleoside or nucleoside/non-nucleoside polymer and a second molecule which comprises a conjugation partner. Such conjugation partners may comprise intercalators, alkylating agents, binding substances for cell surface receptors, lipophilic agents, nucleic acid modifying groups including photo-cross-linking agents such as psoralen and groups capable of cleaving a targeted portion of a nucleic acid, and the like. Such conjugation partners may further enhance the uptake of the Oligomer, modify the interaction of the Oligomer with the target sequence, or alter the pharmacokinetic distribution of the Oligomer. The essential requirement is that the oligonucleoside or nucleoside/non-nucleoside polymer that the Oligomer conjugate comprises be substantially neutral.

The term "substantially neutral" in referring to an Oligomer refers to those Oligomers in which at least about 80 percent of the internucleosidyl linkages between the nucleoside monomers are nonionic linkages.

The term "neutral alkyl- or aryl- phosphonate Oligomer" refers to neutral Oligomers having neutral internucleosidyl linkages which comprise at least one alkyl- or aryl- phosphonate linkage.

The term "neutral methylphosphonate Oligomer" refers to neutral Oligomers having internucleosidyl linkages which comprise at least one methylphosphonate linkage.

The term "acid resistant" refers to Oligomers which are resistant, in comparison to deoxyribooligo-nucleotides, to acid-catalyzed depurination by hydrolysis of the N-glycosyl bond.

The term "triplet" or "triad" refers a hydrogen bonded complex of the bases of three nucleosides between a base (if single stranded) or bases (if double stranded) of a target sequence, a base of a Second Strand and a Third Strand (if a single stranded target sequence) or a base of a Third Strand (if a double-stranded target).

BRIEF DESCRIPTION OF THE DRAWINGS

FIG. 8 depicts examples of dimers which comprise (a) an oligo-2'-O-methyl-ribonucleoside methylphosphonate, (b) an oligodeoxyribonucleoside methylphosphonate, and (c) an oligodeoxyribonucleoside.

DETAILED DESCRIPTION OF THE INVENTION

Preferred Oligomers

Figure 1:
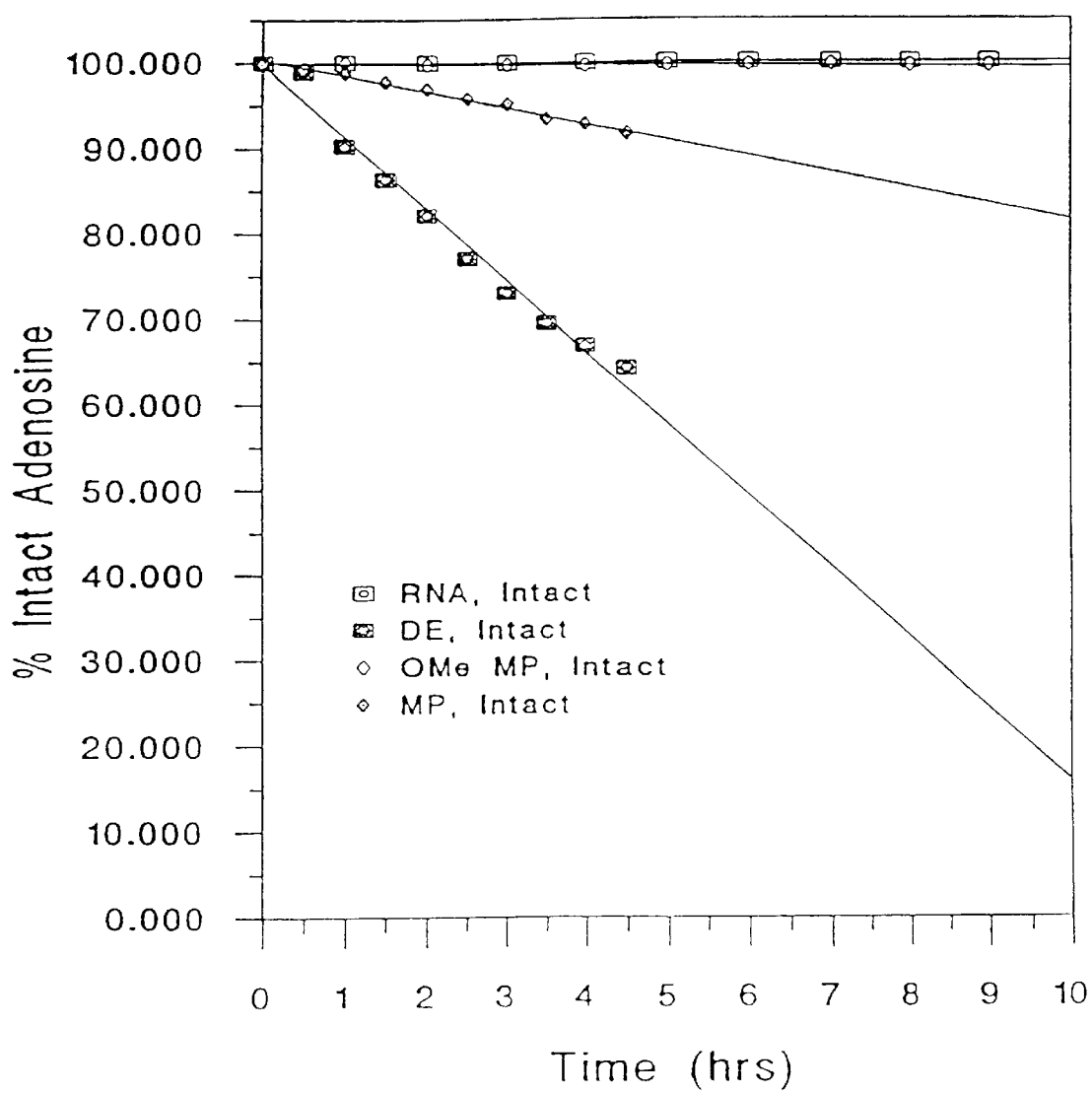
FIG. 1 depicts a plot of the percent intact adenine versus time for Oligomers which comprise RNA, DNA, a methylphosphonate Oligomer having a 2'-O-methyl ribosylant and a methylphosphonate Oligomer.

The Oligomers of the present invention comprise nucleosidyl units having a sugar moiety which is an independently selected 2'-O—alkyl ribosyl group. Suitable are alkyl groups of 1 to 5 carbon atoms. Especially preferred nucleosides have a 2'-O-methyl ribosyl group.

Oligomer Strands having the selected internucleoside linkages may be conveniently prepared according to synthetic techniques known to those skilled in the art. For example, commercial machines, reagents and protocols are available for the synthesis of Oligomers having phosphodiester and certain other phosphorus-containing internucleoside linkages. See also Gait, M. J., *Oligonucleotide Synthesis: A Practical Approach* (IRL Press, 1984); Cohen, Jack S., *Oligodeoxynucleotides Antisense Inhibitors of Gene Expression*, (CRC Press, Boca Raton, FL, 1989); and Oligonucleotides and Analogues: A Practical Approach, (F. Eckstein, ed., 1991). Preparation of Oligomers having certain non-phosphorus-containing internucleoside linkages is described in U.S. Pat. No. 5,142,047, the disclosure of which is incorporated herein by reference.

Preferred are Oligomers that are substantially neutral.

According to an especially preferred aspect, these Oligomers have methylphosphonate internucleosidyl linkages. More preferably all the internucleosidyl linkages are methylphosphonate linkages. Oligomers having a mixture of methylphosphonate internucleosidyl linkage and other nucleosidyl linkages may be preferable for certain therapeutic indications and are intended to be within the scope of the present invention.

Preferably the Oligomer comprise from about 4 to about 40 nucleosides, more preferably, from about 6 to nucleosides. Especially preferred are Oligomer of about 8 to about 20 nucleosides.

Utility and Administration

The Oligomers provided herein may form a high affinity complex with a target sequence such as a nucleic acid or a protein with a high degree of selectivity. For example, derivatized Oligomers may be used to bind with and then irreversibly modify a target site in a nucleic acid by cross-linking (psoralens) or cleaving one or both strands (EDTA). By careful selection of a target site for cleavage, one of the strands may be used as a molecular scissors to specifically cleave a selected nucleic acid sequence.

The Oligomers provided herein may be derivatized to incorporate a nucleic acid reacting or modifying group which can be caused to react with a nucleic acid segment or a target sequence thereof to irreversibly modify, degrade or destroy the nucleic acid and thus irreversibly inhibit its functions.

These Oligomers may be used to inactivate or inhibit or alter expression of a particular gene or target sequence of the same in a living cell, allowing selective inactivation or inhibition or alteration of expression. The target sequence may be DNA or RNA, such as a pre-mRNA or an mRNA. mRNA target sequences include an initiation codon region, a polyadenylation region, an mRNA cap site or a splice junction. These Oligomers could also be used to permanently inactivate, turn off or destroy genes which produced defective or undesired products or if activated caused undesirable effects.

Since the Oligomers provided herein may form duplexes or triple helix complexes or other forms of stable association with transcribed regions of nucleic acids, these complexes are useful in "antisense" or triple strand therapy. "Antisense" therapy as used herein is a generic term which includes the use of specific binding Oligomers to inactivate undesirable DNA or RNA sequences in vitro or in vivo.

Many diseases and other conditions are characterized by the presence of undesired DNA or RNA, which may be in certain instances single stranded and in other instances in double stranded. These diseases and conditions can be treated using the principles of antisense therapy as is generally understood in the art. Antisense therapy includes targeting a specific DNA or RNA target sequence through complementarity or through any other specific binding means, in the case of the present invention by formation of duplexes or triple helix complexes.

The Oligomers for use in the instant invention may be administered singly, or combinations of Oligomers may be administered for adjacent or distant targets or for combined effects of antisense mechanisms with the foregoing general mechanisms.

In therapeutic applications, the Oligomers can be formulated for a variety of modes of administration, including oral, topical or localized administration. It may be beneficial to have pharmaceutical formulations containing acid resistant Oligomers that may come in contact with acid conditions during their manufacture or when such formulations may themselves be made acidic, to some extent, in order to more compatible with the conditions prevailing at the site of application, e.g., the acid mantle of the skin. Techniques and formulations generally may be found in *Remington's Pharmaceutical Sciences*, Mack Publishing Co., Easton, Pa., latest edition. The Oligomer active ingredient is generally combined with a carrier such as a diluent or excipient which may include fillers, extenders, binding, wetting agents, disintegrants, surface-active agents, erodable polymers or lubricants, depending on the nature of the mode of administration and dosage forms. Typical dosage forms include tablets, powders, liquid preparations including suspensions, emulsions and solutions, granules, and capsules.

The Oligomers of the present invention are particularly suited for oral administration which may require exposure of the drug to acidic conditions in the stomach for up to about 4 hours under conventional drug delivery conditions and for up to about 12 hours when delivered in a sustained release from. For treatment of certain conditions it may be advantageous to formulate these Oligomers in a sustained release form. U.S. Pat. No. 4,839,177 to Colombo et al., the disclosure of which is incorporated herein by reference, describes certain preferred controlled-rate release systems. For oral administration, the Oligomers are formulated into conventional as well as delayed release oral administration forms such as capsules, tablets, and liquids.

These Oligomers may be particularly suited for formulation in preparations for topical administration, since the skin has an acid mantle, formulations including these acid resistant Oligomers may prove advantageous. This also can be advantageous in light of the finding that these Oligomers will cross skin and mucous membranes as described in U.S. Patent Application Ser. No. 07/707,879 which is incorporated by reference. Also it may be desirable to provide formulations which include acidic media.

For topical administration, the Oligomers for use in the invention are formulated into ointments, salves, eye drops, gels, or creams, as is generally known in the art.

Systemic administration can also be by transmucosal or transdermal means, or the compounds can be administered orally. For transmucosal or transdermal administration, penetrants appropriate to the barrier to be permeated are used in the formulation. Such penetrants are generally known in the art, and include, for example, bile salts and fusidic acid derivatives for transmucusal administration. In addition, detergents may be used to facilitate permeation. Transmucosal administration may be through use of nasal sprays, for example, as well as formulations suitable for administration by inhalation, or suppositories.

To assist in understanding the present invention, the following examples are included which describe the results of a series of experiments. The following examples relating to this invention should not, of course, be construed in specifically limiting the invention and such variations of the invention, now known or later developed, which would within the purview of one skilled in the art are considered to fall within the scope of the present invention as hereinafter claimed.

EXAMPLES

Example 1

Synthesis of 2' O-Methyladenosine Synthesis Reagents

A. Preparation of 5'-O-Dimethoxytrityl-2'-O-methyl-3'-O-(N,N-diisopropylamino-O-β-cyanoethylphosphine)-N-benzoyladenosine 5'-O-Dimethoxytrityl-2'-O-methyl-N-benzoyladenosine (0.75 g; 1.09 mmoles) (Barry Associates, Inc.) was co-evaporated 3 times with anhydrous 1/1 acetonitrile/ diisopropylethylamine. The nucleoside was then dissolved in 30 ml anhydrous acetonitrile. Diisopropylethylamine (0.570 ml; 3.27 mmoles; 3 eq.) (Aldrich) was added at room temperature followed by chloro-N,N-diisopropylamino-β-cyanoethoxyphosphine (0.386 ml; 1.64 mmoles; 1.5 eq.) (ABN). After one hour the reaction was complete as determined by TLC on silica gel plates using 50/45/5 ethylacetate/hexane/triethylamine as the eluent. The solvent was evaporated, the residue dissolved in dichloromethane, washed with saturated aqueous sodium bicarbonate, and the organic layer dried with anhydrous magnesium sulfate. The crude mixture was purified on a silica gel column that was previously treated with triethylamine to neutralize the acidity of the silica. The product was eluted with 50/49/1 ethylacetate/hexane/triethylamine. The pure fractions were pooled and dried yielding 440 mg (0.45 mmoles; 41.4%) of product.

B. Preparation of 5'-O-Dimethoxytrityl-2'-O-methyl-3'-O-(N N-diisopropylamino-methylphosphine)-N-benzoyladenosine 5'-O-Dimethoxytrityl-2'-O-methyl-N-benzoyladenosine (1.0 g; 1.45 mmoles) (Barry Associates, Inc.) was co-evaporated 3 times with anhydrous 1/1 acetonitrile/ diisopropylethylamine. The nucleoside was dissolved in 20 ml anhydrous acetonitrile. Diisopropylethylamine (1.11 ml; 6.4 mmoles; 4.4 eq.) (Aldrich) was added at room temperature followed by chloro-N,N-diisopropyl-amino-methylphosphine (0.582 ml; 3.2 mmoles; 2.2 eq.) (JBL Scientific). After one hour the reaction was complete as determined by TLC on silica gel plates using 50/45/5 ethylacetate/hexane/triethylamine as the eluent. The solvent was evaporated, the residue dissolved in dichloromethane, washed with saturated aqueous sodium bicarbonate, and the organic layer dried with anhydrous magnesium sulfate. The crude mixture was purified on a silica gel column that was previously treated with triethylamine to neutralize the acidity of the silica. The product was eluted with 50/49/1 ethylacetate/hexane/triethylamine. The pure fractions were pooled and dried yielding 340 mg (0.41 mmoles; 28%) of product.

Example 2

Preparation of a Deoxyadenosine Tetramer Having Phosphodiester Internucleosidyl Linkages (Compound 1)

The tetramen was synthesized and deprotected using standard phosphoramidite procedures (see, e.g., Gait, M.J., *Oligonucleotide Synthesis A Practical Approach*, 1984 (IRL Press) on a Milligen 8750 DNA synthesizer. The compound was purified using reverse-phase HPLC on a Whatman RAC II analytical column and a gradient of acetonitrile ("ACN") in 0.1 M triethylammonium acetate (0–30% ACN over 40 minutes at a flow of 1 ml/minute).

Example 3

Preparation of a Deoxyadenosine Methylphosphonate Tetramer (Compound 2) and a 2'-O-Methyl Adenosine Methylphosphonate Tetramer (Compound 4)

Compound 2 was synthesized using 5'-(dimethoxytrityl) adenosine-3'-[(N,N-diisopro-pylamino)methyl]-phosphonoamite monomer. Solid-phase synthesis was performed on methacrylate polymer supports with a Biosearch Model 8750 DNA synthesizer according to the manufacturer's recommendations except for the following modifications: the monomer was dissolved in acetonitrile at a concentrations of 100 mM. DEBLOCK reagent=2.5% dichloroacetic acid in dichloromethane. OXIDIZER reagent=25 g/L iodine in 0.25% water, 25% 2,6-lutidine, 72.5% tetrahydrofuran. CAP A=10% acetic anhydride in acetonitrile. CAP B=0.625% N,N-dimethylaminopyridine in pyridine. The coupling time was extended to 4 minutes.

The dimethoxytriyl group was removed from the oligonucleotide at the end of the synthesis.

The oligonucleotide was then cleaved from the support and deprotected. The support bound oligonucleotide was removed from the synthesis cartridge and placed in a glass 1 dram vial with a screw top. The support was treated for 30 minutes at room temperature with 1 ml of a solution of acetonitrile/ethanol/NH$_4$OH (9/9/1). Then, 1 ml of ethylenediamine was added to the reaction vessel and the reaction allowed 6 hours to go to completion. The supernatant containing the oligonucleotide was then removed from the support and the support rinsed twice with 2 ml of 1/1 acetonitrile/water, when combined with the supernatant. The combined solution was diluted to 30 ml total volume with water and neutralized with approximately 4 ml of 6 N HCL. The neutralized solution was desalted using a Waters C-18 Sep-Pak cartridge which was pre-equilibrated with 10 ml acetonitrile, 10 ml of 50% acetonitrile/100 mM triethylammonium bicarbonate, and 10 ml of 25 mM triethylammonium bicarbonate, sequentially. After the reaction solution was passed through the column it was washed with 30 ml of water. The product was then eluted with 5 ml of 1/1 acetonitrile/water.

The oligonucleotide was purified by HPLC on a reverse phase column (Whatman RAC II) using a gradient of acetonitrile in 50 mM triethylammonium acetate.

Compound 4 was synthesized, deprotected, and purified as described for Compound 2 using the 2'-O-methyl adenosine monomer of Example 1(B) with the exception that the coupling time was extended to 3 minutes to allow adequate coupling of the more sterically hindered 2'-O-methyl monomer reagent. Compound 4 was synthesized on support bound deoxyadenosine.

Example 4

Preparation of a Adenosine Oligoribonucleotide Tetramer (Compound 3)

The oligoribonucleotide tetramer (Compound 3) was synthesized using 5'-O-dimethoxytrityl-2'-O-tert-butyldimethylsilyl-3'-O-N,N-diisopropyl-β-cyanoethylphosphoramidite adenosine (Millipore). The synthesis was done on a 1 μmole scale with a Milligen 8750 automated DNA synthesizer using standard Milligen phosphoramidite procedures with the exception that the coupling times were extended to 12 minutes to allow adequate time for the more sterically hindered 2'-O-tert-butyldimethylsilyl RNA monomer to react. The syntheses were begun on control-pore glass bound 2'-O-tert-butyldimethylsilyl adenosine (Pennisula Laboratories). All other oligonucleotide synthesis reagents were as described in Milligen's standard protocols. After synthesis, the oligoribonucleotides were handled under sterile, RNases-free conditions. Water was sterilized by overnight treatment with 0.5% diethylpyrocarbonate followed by autoclaving. All glassware was baked for at least 4 hours at 300° C. The oligonucleotides were deprotected and cleaved from support by first treating the support bound Oligomer with 3/1 ammonium hydroxide/ethanol for 15 hours at 55° C. The supernatant, which contained the oligonucleotide, was then decanted and evaporated to dryness. The resultant residue was then treated with 0.6 mL of 1 M tetrabutylammonium fluoride in tetrahydrofuran (which contained 5% or less water) (Aldrich) for 24 hours at room temperature. The reaction was quenched by the addition of 0.6 mL of aqueous 2 M triethylammonium acetate, pH 7. Desalting of the reaction mixture was accomplished by passing the solution through a 10DG column (Bio-Rad) using sterile water. The desalted oligonucleotide was then dried. The compound was purified on HPLC as described for Compound 1 (see Example 2).

Example 5

Preparation of a 2'-O-methyl Adenosine Oligotide Tetramer Having Phosphodiester Internucleosidyl Linkages This oligonucleotide was synthesized, deprotected, and purified as described for compound 1 with the exception that the coupling time was extended to 4 minutes to allow adequate coupling of the more sterically hindered 2'-O-methyl reagent. The compound was synthesized on support bound deoxyadenosine.

Example A

Determination of Acid Stability of Oligomers

The relative stability of Compounds 1 through 5 under acidic conditions that stimulate the pH of the stomach was measured. The compounds were treated with a solution of aqueous HCl, pH 1, and the rate of glycosidic bond cleavage over time determined by the appearance of the digestion product adenine on reverse-phase HPLC chromatograms.

The reverse phase HPLC analyses were performed on a Beckman System Gold HPLC Model 126 pumps, Model 168 photodiode array detector, and Model 507 autoinjector. A Whatman RAC II ODS 3 (100×4.6 mm) analytical column was used for the analyses. The solvent system used was a gradient of acetonitrile in 0.1 M aqueous triethylammonium acetate, pH 7. The gradient was 0 to 2% acetonitrile over 10 minutes followed by 2 to 60% acetonitrile over 10 additional minutes. The gradient then returns to 0% acetonitrile to equilibrate the column for the next injection. The flow rate was 1 ml/minute. This gradient cleanly resolved adenine from the starting reagent and various side-products of the acid digestion.

A 100 ml stock of 0.1 M HCl, pH 1.05, was prepared in sterile water (see above for sterilization protocol) and HPLC analyzed to ensure that the region that adenine elutes was clear of baseline interference. The baseline was clean in the desired region.

The rates of depurination of the tetramers were then determined by dissolving 1 O.D. Unit$_{260}$ with 110 μl injected to obtain the zero hour time point. After that 10 μl samples were automatically sampled at either 0.5 hour intervals (compounds 1 and 2) or 1 hour intervals (compounds 3 through 5). Results are set forth in Table I below.

Figure 2:
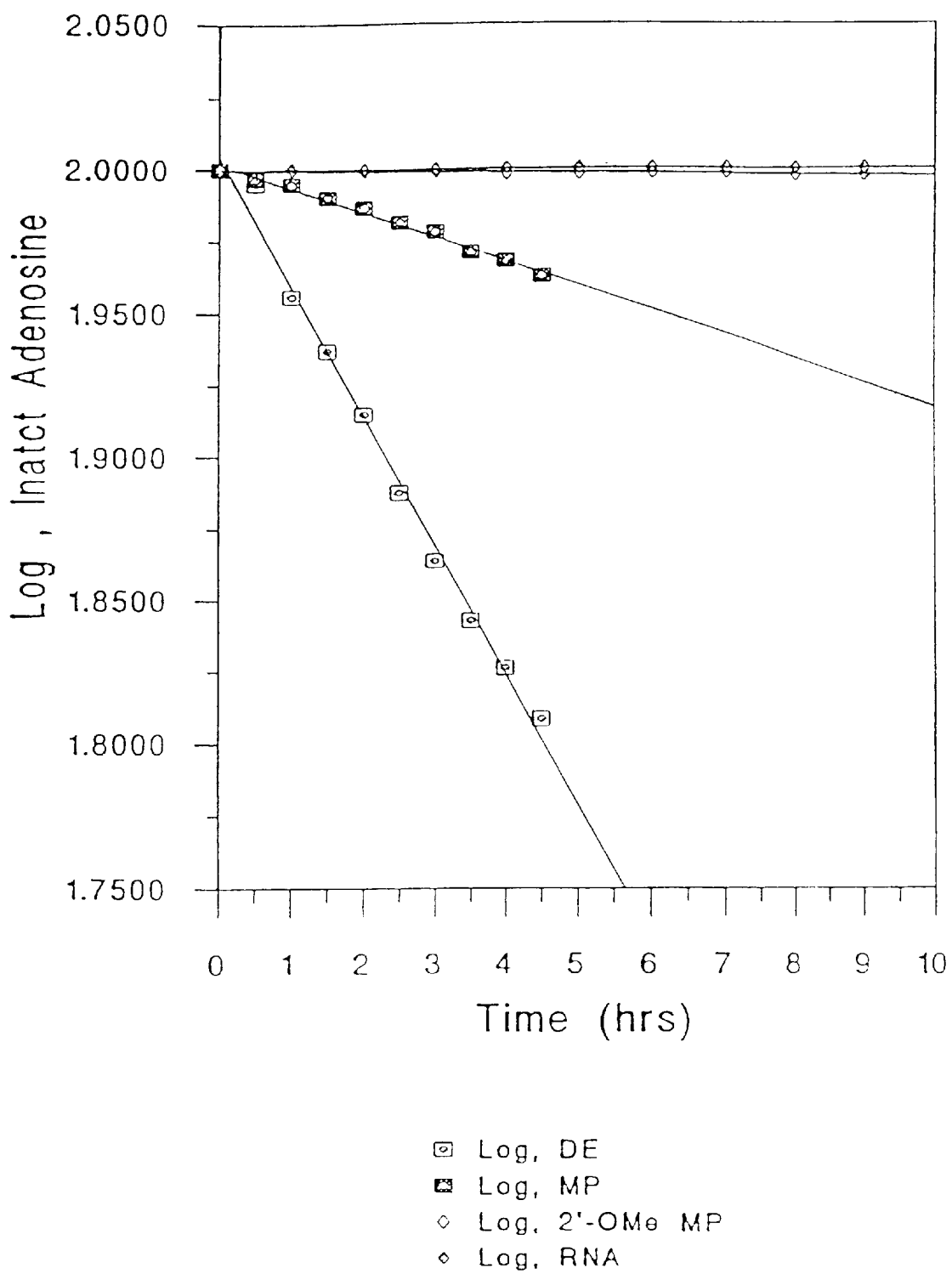
FIG. 2 depicts a plot of the log of the percent intact adenine versus time for the same Oligomers as plotted in FIG. 1.

FIG. 1 depicts a plot of the percent intact adenosine versus time for the tetramers. FIG. 2 is a plot of the log of the percent intact adenosine versus time. From the log plot the k$_A$'s and half-lives of the rates of depurination of the tetramers were calculated. Table 1 contains those figures, as well as the relative rates of depurination as compared to the phosphodiester control (compound 1).

TABLE I

| Compound No. | Rate Constant (sec$^{-1}$) @ 20° C. | t1/2 (hrs) | Relative Rates of Depurination |
|---|---|---|---|
| 1 (phosphodiester) | 374.4 | 6.66 | 1.00 |
| 2 (methylphosphonate) | 70.56 | 35.66 | 0.188 |
| 3 (RNA) | Not measurable (<1) | Not measurable (>3000) | Not measurable (<0.001) |
| 4 (2' OMe methylphos.)* | 2.16 | 1155 | 0.0057 |

*Corrected for 3'-terminal deoxyadenosine.

The results clearly demonstrate that 2' O-methyladenosinyl methylphosphonates are vastly more stable (175x) than either the phosphodiester deoxyadenosine or methylphosphonate deoxyadenosine analogs. The small amount of depurination evident with the 2' O-methyladenosinyl methylphosphonate is most likely due to the 3' terminal nucleoside which is a deoxyadenosinyl residue instead of 2' OMe adenosinyl, which is not available on support. To illustrate the difference in depurination rates, after 4 hours of treatment at pH 1 about 33% of the phosphodiester deoxyadenosines, only 7% of the methylphosphonate deoxyadenosines, and just 0.28% of the 2' O-methyladenosine methylphosphonates have depurinated.

A very surprising observation was the stability of the methylphosphonate deoxyadenosinyl tetramer. The stabilizing effect of the phosphonate backbone on the glycosidic bond was unexpected.

Example B

Determination of Acid Stability of Oligomers at 37° C.

The relative stability of Compounds 1 to 4 was determined as described in Example A using a heat block that maintained temperature at 37° C.

Results are set forth in Table II below.

TABLE II

| Compound No. | Rate Constant (sec$^{-1}$) @ 37° C. | t1/2 (hrs) | Relative Rates of Depurination |
|---|---|---|---|
| 1 (phosphodiester) | 1800 | 1.39 | 1.00 |
| 2 (methylphosphonate) | 203.9 | 12.24 | 0.114 |
| 3 (RNA) | Not measurable (<1) | Not measurable (>3000) | Not measurable (<0.001) |
| 4 (2' OMe methylphos.)* | Not measurable (<1) | Not measurable (>3000) | Not measurable (<0.0001) |

*Corrected for 3'-terminal deoxyadenosine.

Figure 3:
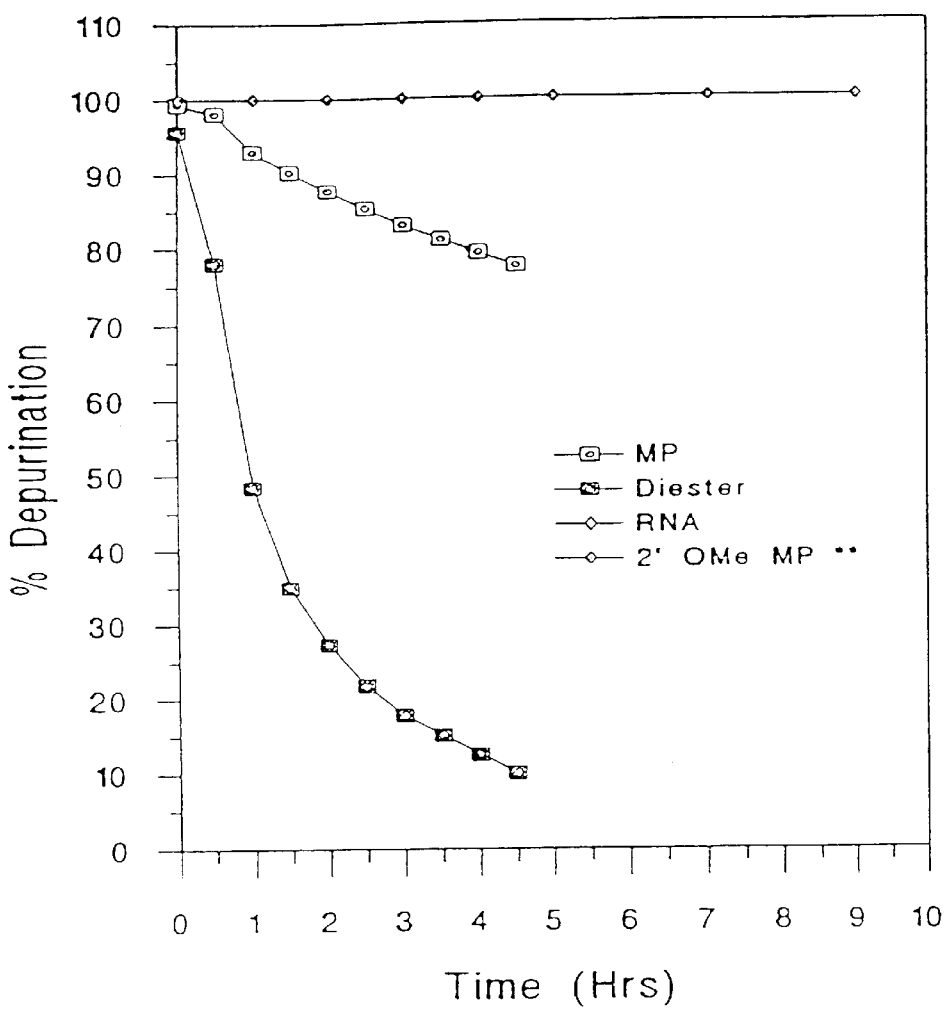
FIG. 3 depicts a plot of the percent depurination versus time at 37° C. for Oligomers which comprise RNA, DNA, a methylphosphonate Oligomer having a 2'-O-methylribosyl units and a metholphosphonate Oligomer.
Figure 4:
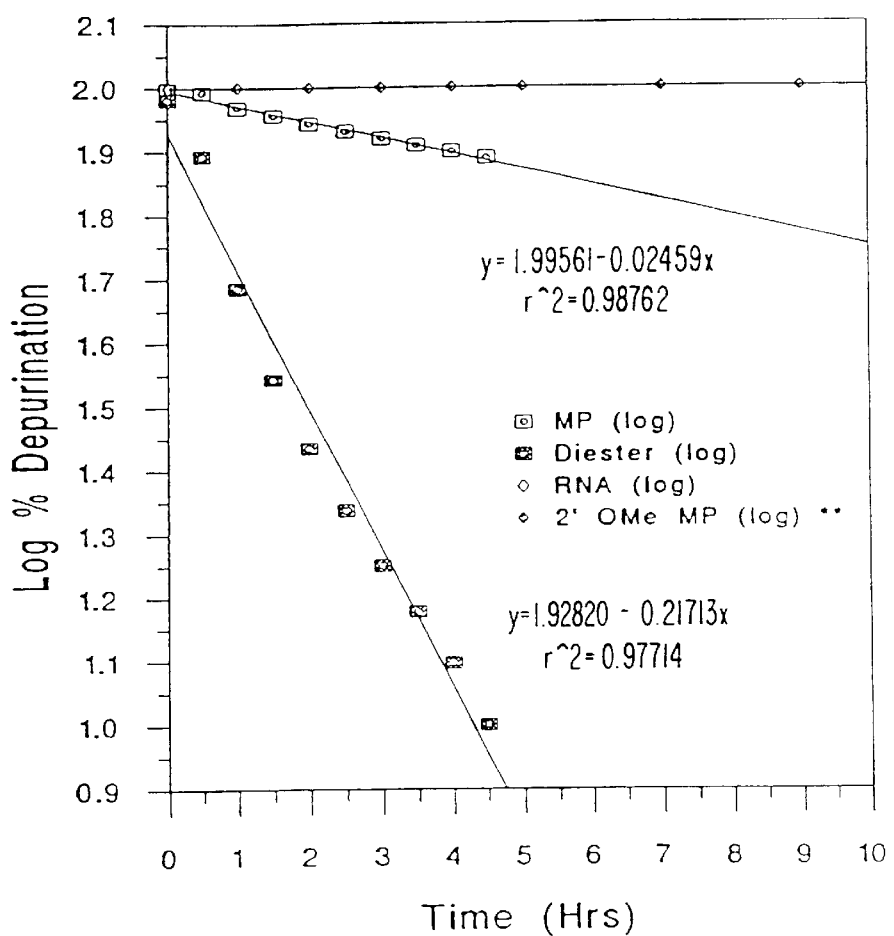
FIG. 4 depicts a plot of the log of the percent depurination versus time at 37° C. for the same Oligomers as plotted in FIG. 3.
Figure 5:
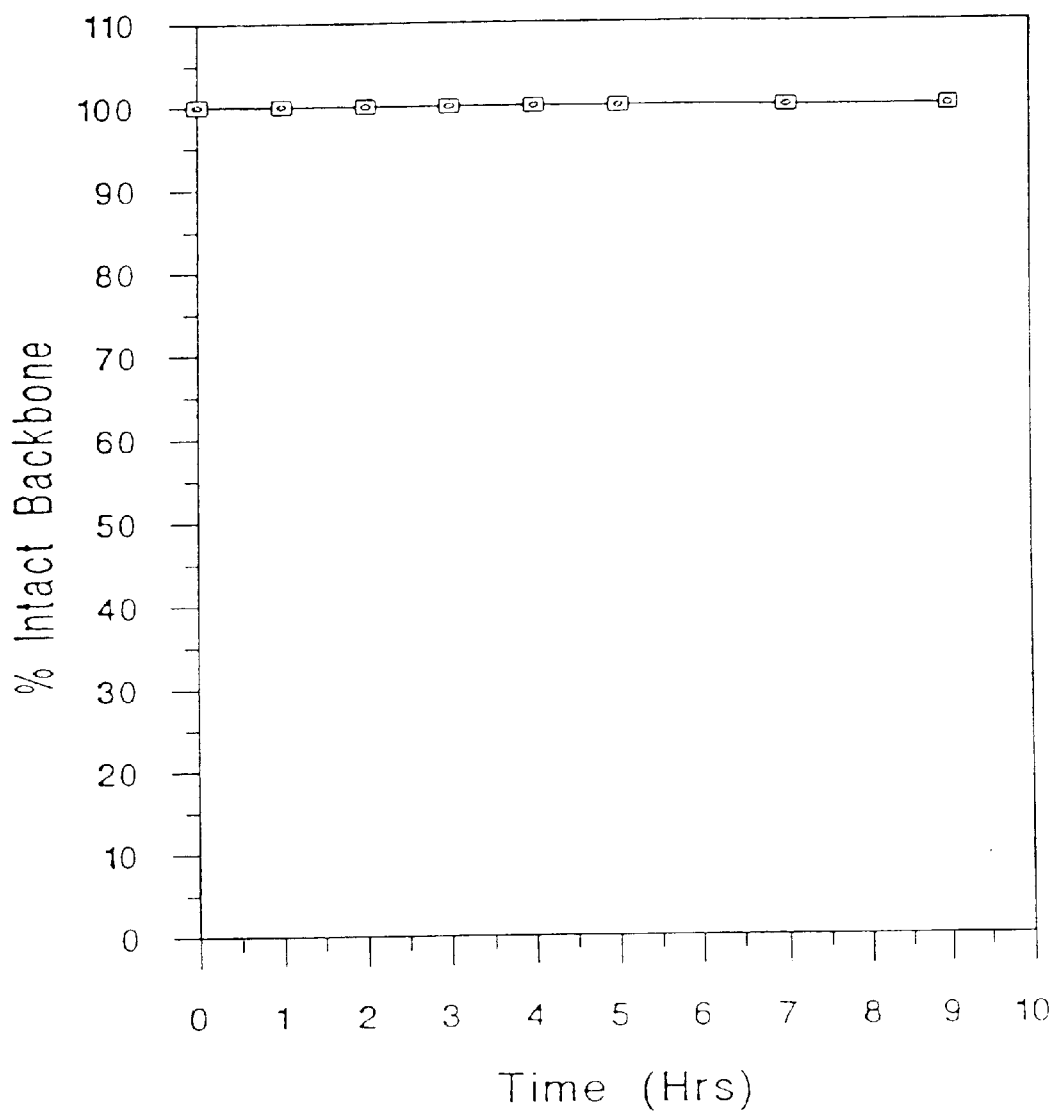
FIG. 5 depicts a plot of percent intact backbone versus time for a methylphosphonate Oligomer having 2'-O-methyl ribosyl units at 37° C. and pH 1.

FIG. 3 depicts the rate of depurination of the adenosinyl tetramers at pH 1.0 and 37° C. plotted as percent depurination versus time. FIG. 4 depicts the rate of depurination of adenosinyl tetramers at pH 1.0 and 37° C. plotted as log percent depurination versus time. FIG. 5 depicts stability of the methylphosphonate backbone to acidic conditions at pH 1.0 and 37° C. for the (2'-O-methyl A)$_3$(dA)-methylphosphonate Oligomer. The conditions were 0.3 mM Oligomer in 0.1 M HCl, pH 1.0 at 37° C. Limit of detection was 0.2%; error was <2%. Rate was determined by increase of free adenine compared with total adeninyl bearing species, which was followed by HPLC. Data were corrected for depurination, and cleavage of 3'-terminal deoxyadenosine for the 2'-O-methyladenosinyl methylphosphonate Oligomer.

Example C

Acid Stability of a Oligo-2'-O-Methylribonucleoside Methylphosphonate

An oligo-2'-O-methylribonucleoside methylphosphonate (A) was prepared using suitably protected 2'-O-methylribonucleoside methylphosphonamidite synthone. In the notation indicated below, N$^m$ indicates a 2'-O-methylribonucleoside, and the underline indicates the positions of the methylphosphonate linkages. The 5'-internucleotide bond of the Oligomer is a phosphodiester linkage. The Oligomer was deprotected by sequential treatment with hydrazine hydrate in pyridine buffered with acetic acid, followed by treatment with a solution of ethylenediamine in 95% ethanol (1:1 v/v). The Oligomer was purified by DEAE cellulose chromatography, followed by preparative HPLC on a C-18 reversed phase column.

| | |
|---|---|
| r-AU$^m$A$^m$G$^m$G$^m$A$^m$U$^m$U$^m$U$^m$G$^m$U$^m$C | A |
| d-ATAGGATTGTC | B |
| d-ATAGGATTGTC | C |

Oligomer A was phosphorylated using polynucleotide kinase and gamma- [$^{32}$P] -ATP. The phosphorylated Oligomer was then incubated with 0.1 N HCl or 1.0 N HCl at 37° C. overnight (~14 hours). The Oligomer was then analyzed by polyacrylamide gel electrophoresis under denaturing conditions. No degradation of the Oligomer was detected under these conditions. According to our experience, incubation of the deoxyribonucleoside methylphosphonate (B) with 0.1 N HCl overnight at 37° C. or with 1.0 N HCl at 37° C. for several hours would result in considerable depurination at the G and A nucleosides. This depurination would be followed by spontaneous hydrolysis of the methylphosphonate linkages resulting in production of shorter chain-length Oligomers. Past experience has shown that purine residues in oligodeoxyribonucleotides such as (C) are even more sensitive to acid-catalyzed depurination.

The results of these experiments thus suggest that purine nucleosides in an oligo-2'-O-methylribonucleoside methylphosphonate are much more resistant to acid catalyzed depurination than are the corresponding purine nucleosides in oligodeoxyribonucleoside methylphosphonates or oligodeoxyribonucleosides. The apparent resistance of oligo-2'-O-methylribonucleoside methylphosphonates to acid catalyzed depurination could have important therapeutic consequences, particularly if these Oligomers were to be administered orally.

Example D

Figure 6:
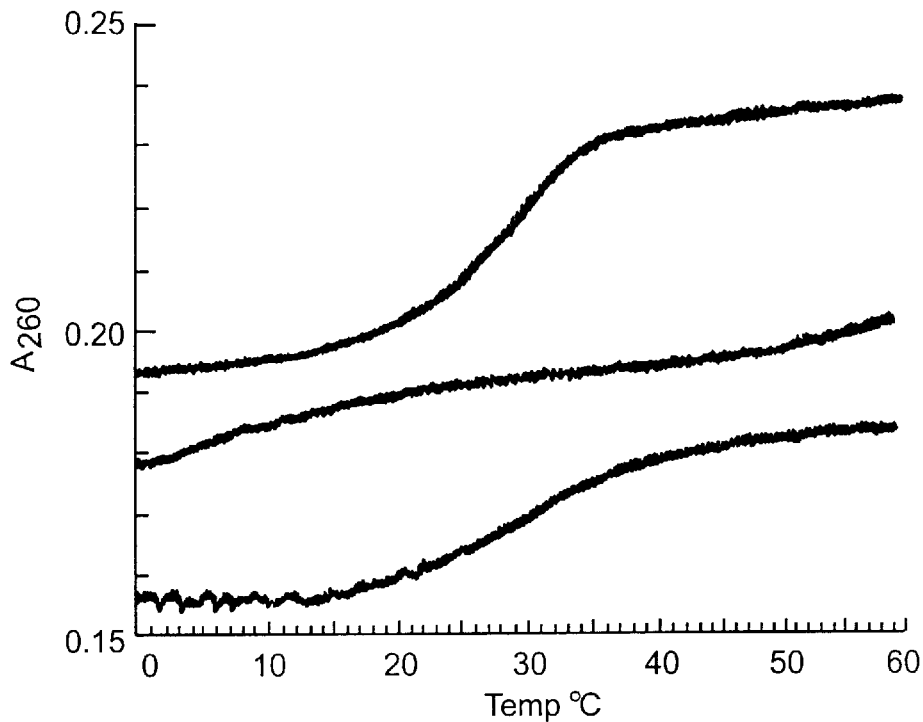
FIG. 6 depicts a melting curve for hybridization of Oligomers which comprise an oligodeoxyribonucleotide (1), a methylphosphonate Oligomer having 2'-O-methylribosyl units (2) and a methylphosphonate Oligomer having deoxyribosyl units (3) with a DNA target.
Figure 7:
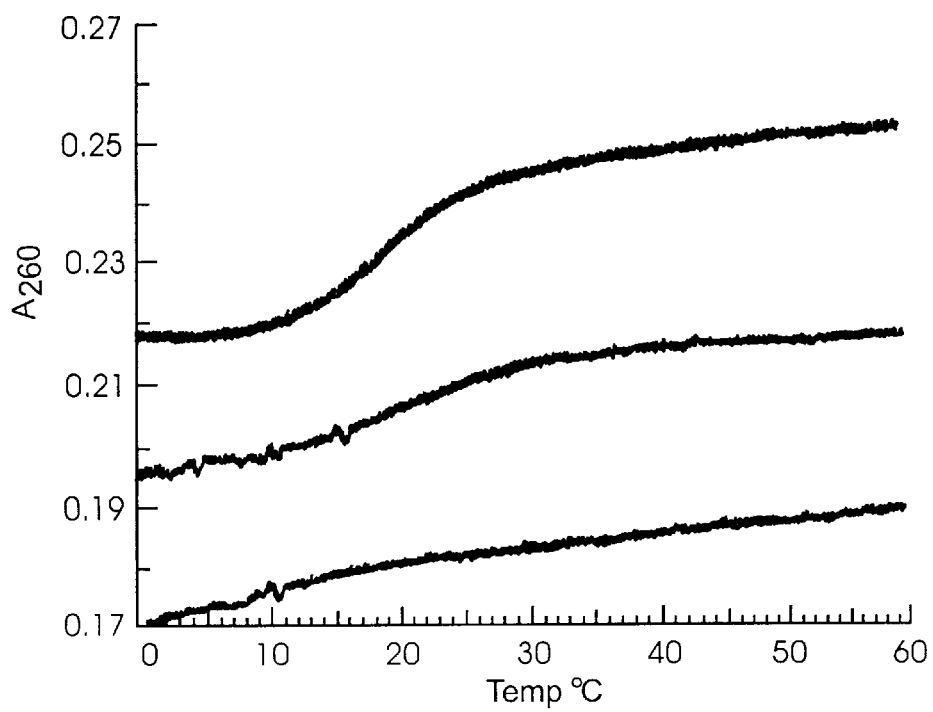
FIG. 7 depicts a melting curve for hybridization of the same Oligomers as FIG. 6 with an RNA target.

Hybridization of a Oligo-2'-O-Methylribonucleoside Methylphosphonate to Complementary DNA and RNA Targets The hybridization properties of Oligomer 2 was determined and compared to those of Oligomers 1 and 3. Hybridization to complementary single-stranded DNA target D or RNA target E was carried out in a buffer containing 10 mM HEPES (pH 7.0), 2 mM EDTA. The resulting melting curves and melting temperatures are shown in FIGS. 6 and 7 (note: in these figures, N$^m$ represents a 2'-O-methylribonucleoside). The oligodeoxyribonucleotide, 1, formed stable hybrids with both the DNA and RNA targets. The oligo-2'-O-methylribonucleoside methylphosphonate, 2, did not hybridize with DNA target, but did form a very stable duplex with the RNA target. This behavior is in contrast to that of the oligodeoxyribonucleoside methylphosphonate, 3, which forms a stable duplex with the DNA target, but only a very weak duplex with the RNA target. These results suggest that oligo-2'-O-methylribonucleoside methylphosphonates may form more stable hybrids with RNA than do oligodeoxyribonucleoside methylphosphonates and thus they be more effective antisense reagents when targets against cellular or viral RNAs.

TABLE III

|  |  | Tm |
|---|---|---|
| d-G A C A A A T C C T A T (DNA TARGET) |  |  |
| C T G T T T A G G A T A-d | 1 | 28° C. |
| CU*G*U*U*U*A*G*G*A*U*A-r | 2 | <0° C. |
| CTGTTTAGGATA-d | 3 | 30° C. |

Buffer: 10 mM HEPES pH 7.0
2 mM EDTA

TABLE IV

|  |  | Tm |
|---|---|---|
| r-G A C A A A U C C U A U (RNA TARGET) |  |  |
| C T G T T T A G G A T A-d | 1 | 18° C. |
| CU*G*U*U*U*A*G*G*A*U*A-r | 2 | 20° C. |
| CTGTTTAGGATA-d | 3 | <0° C. |

Buffer: 10 mM HEPES pH 7.0
2 mM EDTA

We claim:

1. A pharmaceutical composition which retains its chemical structure under acidic conditions which comprises a effective amount of an acid resistant antisense Oligomer in a carrier.

2. A composition according to claim 1 wherein said acid resistant Oligomer is a 2'-O-alkyl ribosyl substituted Oligomer of preselected base sequence.

3. A composition having enhanced stability in an acid environment which comprises a 2'-O-alkyl ribosyl nucleosidyl substituted Oligomer of a preselected base sequence and a carrier.

4. A composition according to claim 3 wherein said antisense Oligomer further comprises about 80 percent to 100 percent nonionic internucleosidyl linkages.

5. A composition according to claim 3 wherein said oligomer has at least one purine base.

6. A composition according to claim 3 wherein said antisense Oligomer further comprises methylphosphonate internucleosidyl linkages.

7. A composition according to claim 6, wherein said 2'-O-alkyl is 2'-O-methyl.

8. A composition according to claim 7 wherein said antisense Oligomer further about 50 to 100 percent methylphosphonate internucleosidyl linkages.

9. A method of synthesizing a methylphosphonate Oligomer of a preselected base sequence with enhanced resistance to acid degradation compared with a 2'-deoxyoligonucleotide of the same base sequence which comprises sequentially coupling phosphonoamidite nucleosidyl monomers to give an Oligomer having methylphosphonate internucleosidyl linkages.

10. A method according to claim 9 wherein about 50 to 100 percent of said internucleosidyl linkages are methylphosphonate internucleosidyl linkages.

11. A method of synthesizing a 2'-O-alkyl ribosyl nucleosidyl substituted Oligomer of a preselected base sequence with enhanced resistance to acid degradation compared with a 2'-deoxyoligonucleotide of the same base sequence which comprises sequentially coupling 2'-O-alkyl ribosyl phosyhonoamidite or phosphoramidite nucleosidyl monomers to give an Oligomer having internucleosidyl linkages selected from methylphosphonate, phosphodiester and phophonothiote internucleosidyl linkages.

12. A method according to claim 11 wherein said Oligomer further comprises about 80 percent to 100 percent nonionic internucleosidyl linkages.

13. A method according to claim 11 wherein at least one of said internucleosidyl linkages is a methylphosphonate internucleosidyl linkage.

14. A method according to claim 11 wherein said 2'-O-alkyl ribosyl nucleosidyl substituted Oligomer is a 2'-O-methyl ribosyl nucleosidyl substituted Oligomer.

15. A method according to claim 11 wherein said Oligomer further comprises about 50 percent to 100 percent methylphosphonate internucleosidyl linkages.

* * * * *

UNITED STATES PATENT AND TRADEMARK OFFICE
CERTIFICATE OF CORRECTION

PATENT NO. : 6,005,094
DATED : December 21, 1999
INVENTOR(S) : Simon et al.

It is certified that error appears in the above-identified patent and that said Letters Patent is hereby corrected as shown below:

Column 13,
Line 34, "A pharmaceutical composition. . ." should read -- A composition. . . --
Line 35, ". . .comprises a effective. . ." should read -- . . .comprises an effective. . . --
Line 45, before "Oligomer," delete "antisense."

Column 14,
Line 4, before "Oligomer," delete "antisense."
Line 9, before "Oligomer," delete "antisense."
Line 9, "Oligomer further about 50 to 100" should read -- Oligomer further comprises about 50 to 100 --

Signed and Sealed this

Twentieth Day of August, 2002

*Attest:*

JAMES E. ROGAN
*Director of the United States Patent and Trademark Office*

*Attesting Officer*